(12) United States Patent
Kim

(10) Patent No.: US 8,936,543 B2
(45) Date of Patent: Jan. 20, 2015

(54) METHOD OF MANUFACTURING COMPOSITION FOR ENLARGING PENIS AND METHOD OF ENLARGING PENIS USING THE COMPOSITION

(76) Inventor: Jae-Young Kim, Gyeonggi-do (KR)

( * ) Notice: Subject to any disclaimer, the term of this patent is extended or adjusted under 35 U.S.C. 154(b) by 462 days.

(21) Appl. No.: 13/343,678

(22) Filed: Jan. 4, 2012

(65) Prior Publication Data

US 2013/0172668 A1   Jul. 4, 2013

(51) Int. Cl.
*A61K 35/36*      (2006.01)
(52) U.S. Cl.
USPC ............................................. 600/38
(58) Field of Classification Search
CPC ........... A61F 5/00; A61K 35/16; A61K 35/36
USPC ..................... 623/23.72, 23.73, 23.74, 23.75; 604/522; 600/38–41; 128/897, 898
See application file for complete search history.

(56) References Cited

U.S. PATENT DOCUMENTS 7,585,670 B2 *   9/2009   Hedrick et al. ............... 435/325
2007/0122906 A1 *   5/2007   Mishra .......................... 435/372

* cited by examiner

*Primary Examiner* — Samuel Gilbert
(74) *Attorney, Agent, or Firm* — IPLA P.A.; James E. Bame

(57) ABSTRACT

A method of manufacturing a composition for enlarging the penis comprises the steps of picking the auto-tissue of a skin from the abdomen or flank region of a patient; (2) obtaining a purified mixture of the dermis and fat by removing the red blood cells of a lower layer from the auto-tissue through centrifugation; (3) separating and extracting stem cells from part of the purified mixture; (4) picking blood from the patient and purifying the blood through centrifugation; (5) extracting a Platelet Rich Plasma (PRP), including rich growth factors, from the purified blood; and (6) fabricating the composition by mixing the mixture obtained at the step (2) and not used to extract the stem cells, the stem cells, and the Platelet Rich Plasma (PRP).

5 Claims, 4 Drawing Sheets

METHOD OF MANUFACTURING COMPOSITION FOR ENLARGING PENIS AND METHOD OF ENLARGING PENIS USING THE COMPOSITION

BACKGROUND OF THE INVENTION

1. Field of the Invention

The present invention relates to a method of manufacturing a composition for enlarging the penis and a method of enlarging the penis using the composition and, more particularly, to a method of manufacturing a composition for enlarging the penis, wherein a Platelet Rich Plasma (PRP), including the dermis, fat, stem cells, and growth factors extracted from the auto-tissue of a patient, can be transplanted into the penis through a microtubule and an enlargement effect can remain intact after the operation, and a method of enlarging the penis using the composition.

2. Background of the Related Art

In general, an operation of enlarging the penis of the male includes a method of inserting solid silicone after local anesthesia, a method of transplanting auto-dermis fat, etc. The penis is a part that has the greatest body contact and the strongest friction during a sexual life process. Accordingly, a penis enlargement operation employing an auto-dermis fat transplantation operation and special material for an artificial blood vessel rather than a silicone injection operation has been in the spotlight as a very safe, permanent, and practical method.

A common 'penis enlargement operation' refers to an operation of transplanting own dermis fat. The dermis fat transplantation operation method includes ripping off dermis fat from a hip or the abdomen incising the upper part of the penis, transplanting the ripped dermis fat, and suturing the incision area. The existing operation method, however, is problematic in that a permanent scar (i.e. an operation mark) remains because the penis is incised and a sutured part bursts when the penis erects.

Furthermore, about 5% of patients who have been operated experiences an inflammation generated in a penis sutured part, the necrosis of a transplanted dermis fat tissue, a calcification symptom in which part of a transplanted penis becomes hard, and so on. In particular, if the skin tissue is soft or redundant skin is insufficient in the penis, a probability that side effects may occur in the penis sutured part is relatively high.

Accordingly, the inventors of the present invention have invented a method capable of solving the above problems and enlarging the penis while preventing damage to a nerve or a blood vessel without incising the penis. According to this method, after a pubic area is incised, a composition for enlarging the penis, including the dermis, fat, and stem cells extracted from the auto-tissue of the abdomen or flank region of a patient and a Platelet Rich Plasma (PRP) extracted form the blood of the patient, is inserted into the penis through a pubic area without directly inserting the composition into the penis. Consequently, the penis can be enlarged while obviating side effects without leaving any mark in the penis.

SUMMARY OF THE INVENTION

Accordingly, an object of the present invention is to provide a method of manufacturing a composition for enlarging the penis, wherein a Platelet Rich Plasma (PRP), including the dermis, fat, stem cells, and growth factors extracted from the auto-tissue of a patient, can be transplanted into the penis through a microtubule and an enlargement effect can remain intact after the operation.

Another object of the present invention is to provide a method of enlarging the penis which is capable of leaving any mark in the penis and obviating side effects by using the composition for enlarging the penis and of preventing damage to a nerve or a blood vessel in a penis enlargement process by enlarging the penis while checking a nerve or a blood vessel through a microtubule.

To achieve the above object, method of manufacturing a composition for enlarging the penis according to the present invention includes the steps of (1) picking the auto-tissue of a skin from the abdomen or flank region of a patient; (2) obtaining a purified mixture of the dermis and fat by removing the red blood cells of a lower layer from the auto-tissue, picked at the step (1), through centrifugation; (3) separating and extracting stem cells from part of the mixture of the dermis and fat purified at the step (2); (4) picking blood from the patient and purifying the blood through centrifugation; (5) extracting a Platelet Rich Plasma (PRP), including rich growth factors, from the blood purified at the step (4); and (6) fabricating the composition for enlarging the penis by mixing the mixture of the dermis and fat obtained at the step (2) and not used to extract the stem cells, the stem cells obtained at the step (3), and the Platelet Rich Plasma (PRP) obtained at the step (5).

To achieve the other of the objects, a method of enlarging the penis using a composition for enlarging the penis according to the present invention includes the steps of (1) incising the pubic area of a patient in a length of 1 cm or less up to a hypoderm layer; (2) inserting a microtubule between the epidermis and the hypoderm of the incised part and moving the microtubule to a penis region; (3) when the end of the microtubule is placed at the penis region, injecting the composition for enlarging the penis into the microtubule; and (4) after the composition is injected, suturing the part incised at the step (1).

Preferably, an endoscope 60 is first inserted in order to check whether a nerve or a blood vessel vertically exists in the region of the epidermis 41 and the hypoderm layer 42 between which the microtubule is inserted.

DETAILED DESCRIPTION OF EMBODIMENTS

Technical terms and scientific terms used in the present invention may be interpreted as having meanings typically understood by a person having ordinary skill in the art to which the present invention pertains, unless defined otherwise.

In the present invention, after the abdomen or flank region of a patient is partially anesthetized, the auto-tissue of the skin of 200 cc is picked by using an 8-9 gauge tube. After the red blood cell of a lower layer of the picked auto-tissue of 200 g is removed through centrifugation for 3 to 5 minutes, a purified mixture of 120 cc, including the dermis and fat, is obtained. Type I Collagenase of about 1 g is injected into and mixed with the purified mixture of dermis and fat of 80 cc, a fat layer of an upper layer is removed from the purified mixture through centrifugation, and stem cells of 4 cc is then separated and extracted from the purified mixture through centrifugation. The stem cells of 4 cc may include about 1.6 millions of the stem cells, but may slightly differ according to a person.

Meanwhile, after blood of 20 cc is picked from a patient and purified through centrifugation, a Platelet Rich Plasma (PRP) of 5 cc including rich growth factors is extracted from the purified blood.

The mixture of the dermis and fat of 40 cc, the stem cells of 4 cc, and the Platelet Rich Plasma (PRP) of 5 cc through the above process are mixed to fabricate a composition for enlarging the penis.

A method of enlarging the penis using the composition for enlarging the penis according to the present invention includes incising a region where the pubic hair of the patient is grown in a length of 1 cm or less up to a hypoderm layer, inserting a microtubule between the epidermis and the hypoderm of the incised part, moving the microtubule to a penis region, and injecting the composition for enlarging the penis through the microtubule. After the composition for enlarging the penis is injected, the incised part is sutured.

A method of enlarging the penis using an endoscope according to the present invention is described in detail below with reference to FIGS. 2 to 4.

Figure 1:
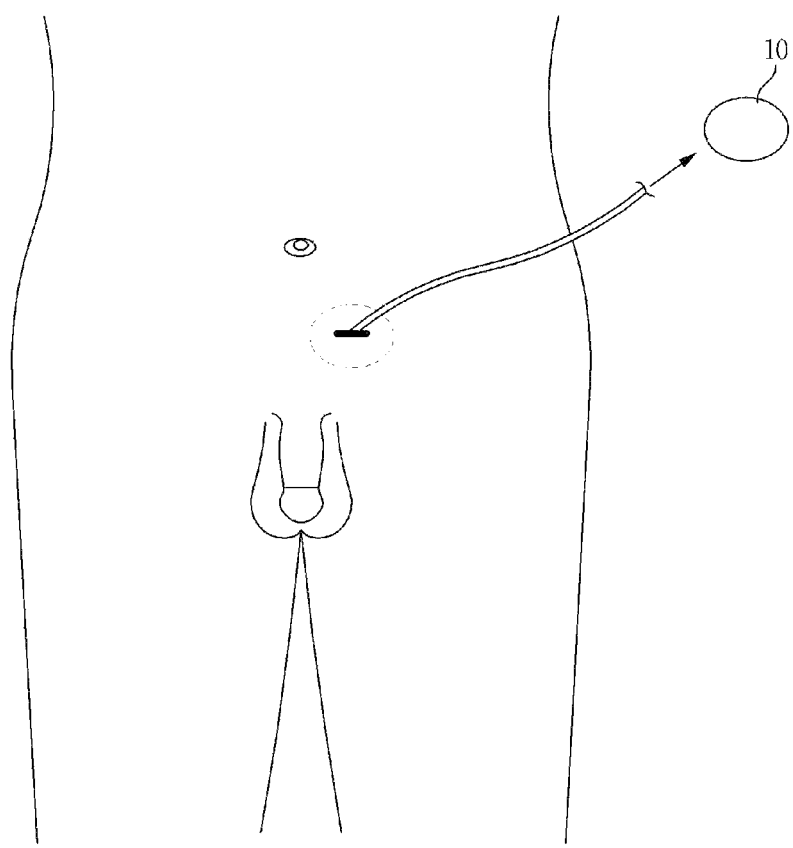
FIG. 1 shows a shape in which the auto-tissue of an abdomen or flank region is picked during a penis enlargement operation according to the present invention.
Figure 2:
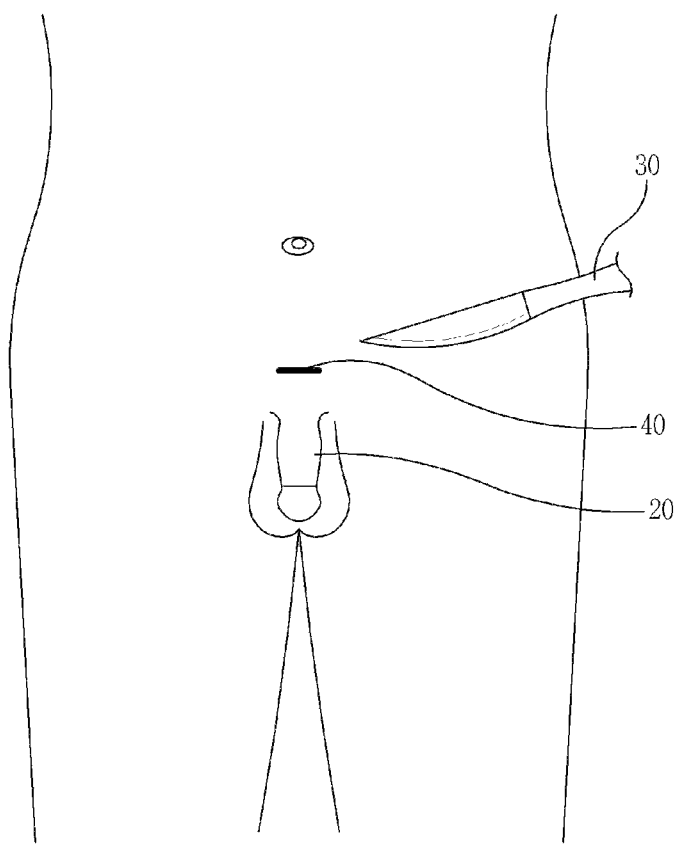
FIG. 2 shows a shape in which the skin of a penis region is incised using a surgical knife during the penis enlargement operation according to the present invention.
Figure 3:
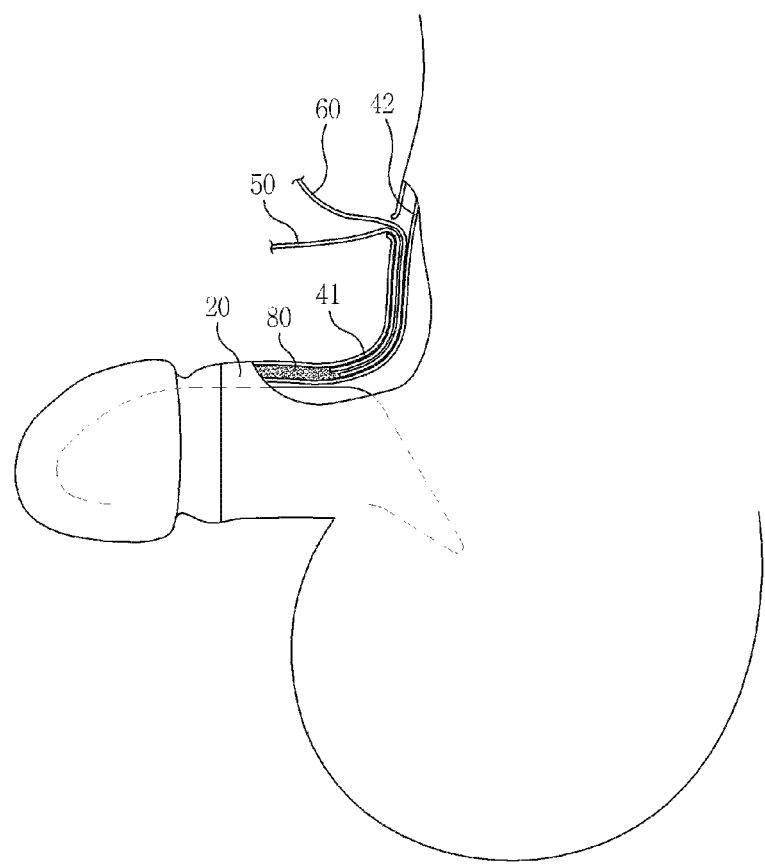
FIG. 3 shows a shape in which a microtubule is inserted during the penis enlargement operation according to the present invention.
Figure 4:
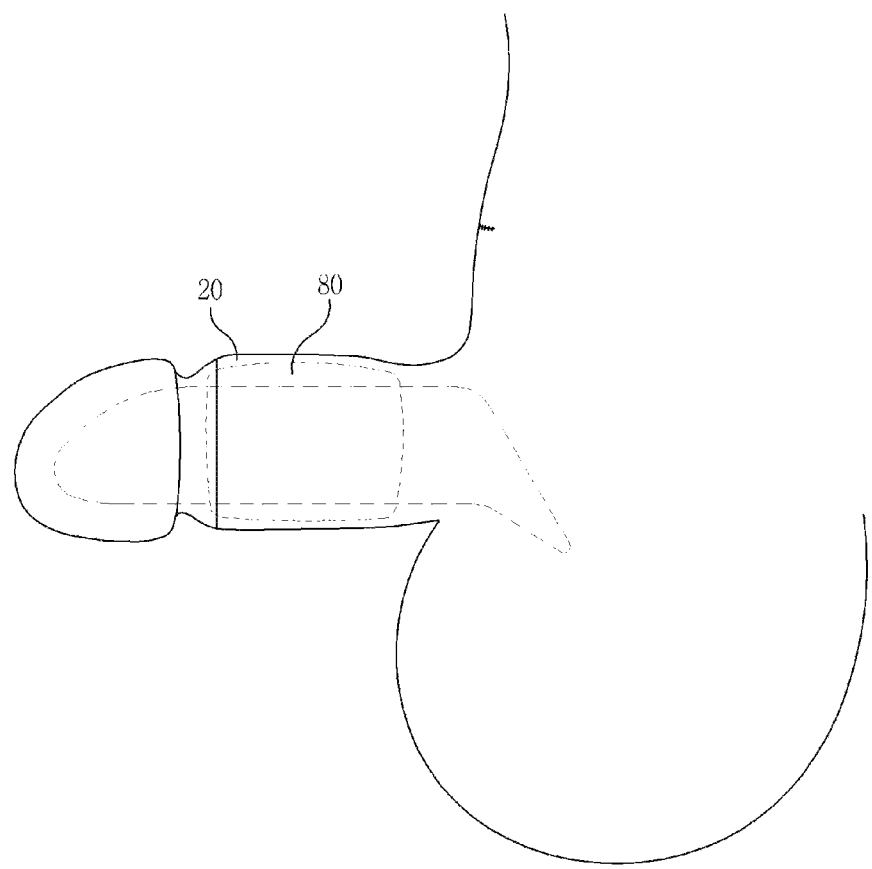
FIG. 4 shows a shape in which a composition for enlarging the penis has been injected during the penis enlargement operation according to the present invention.

FIG. 1 shows a shape in which the auto-tissue of an abdomen or flank region is picked during a penis enlargement operation according to the present invention, FIG. 2 shows a shape in which the skin of a penis region is incised using a surgical knife during the penis enlargement operation according to the present invention, FIG. 3 shows a shape in which a microtubule is inserted during the penis enlargement operation according to the present invention, and FIG. 4 shows a shape in which a composition for enlarging the penis has been injected during the penis enlargement operation according to the present invention.

First, as shown in FIG. 1, dermis fat 10 is picked from the abdomen or the flank. The mixture of the dermis and fat and the stem cells are extracted from the picked dermis fat 10 and then mixed with the Platelet Rich Plasma (PRP) of 5 cc to fabricate the composition for enlarging the penis.

After pubic hair over the penis 20 under the navel in a region where pubic hair is grown is removed, the skin 40 is incised in a length of about 1 cm or less up to a subcutaneous fat layer 42 by using a surgical knife 3 as shown in FIG. 20. After the skin 40, the microtubule 50 is inserted between the epidermis 41 and the hypoderm layer 42 of the region of the penis 20 and the composition for enlarging the penis is injected through the microtubule as shown in FIG. 3. Here, it is preferred that an endoscope 60 be first inserted in order to check whether a nerve or a blood vessel vertically exists in the part of the epidermis 41 and the hypoderm layer 42 between which the microtubule is inserted.

After the composition 80 for enlarging the penis is injected, the incised part is sutured to complete the operation as shown in FIG. 4.

Accordingly, after a pubic area is incised without incising the penis, an operation of enlarging the penis by using an endoscope. Accordingly, the penis can be enlarged while not giving damage to a nerve or a blood vessel.

Furthermore, any scar does not exist in the penis, and the existing operation time can be reduced by half or more because the operation time is finished in 1 hour. Furthermore, medicinal side effects due to anesthesia can be minimized, and there is no side effect because the injected subcutaneous fat is combined with the subcutaneous fat of the penis without a side effect.

As described above, if the composition for enlarging the penis according to the present invention is used, after a pubic area is incised without incising the penis, an auto-tissue picked from the abdomen or the flank region of a patient is injected through the pubic area. Accordingly, there are advantages in that any mark does not exist in the penis and there is no side effect.

Furthermore, the penis is enlarged while checking a nerve or a blood vessel through an endoscope before the composition for enlarging the penis is injected through the microtubule. Accordingly, damage to a nerve or a blood vessel can be prevented in the penis enlargement process.

What is claimed is:
1. A method of manufacturing a composition for enlarging a penis, comprising the steps of:
   (1) picking an auto-tissue of a skin from an abdomen or flank region of a patient;
   (2) obtaining a purified mixture of a dermis and fat by removing red blood cells of a lower layer from the auto-tissue, picked at the step (1), through centrifugation;
   (3) separating and extracting stem cells from part of the mixture of the dermis and fat purified at the step (2);
   (4) picking blood from the patient and purifying the blood through centrifugation;
   (5) extracting a Platelet Rich Plasma (PRP), including rich growth factors, from the blood purified at the step (4); and
   (6) fabricating the composition for enlarging the penis by mixing the mixture of the dermis and fat obtained at the step (2) and not used to extract the stem cells, the stem cells obtained at the step (3), and the Platelet Rich Plasma (PRP) obtained at the step (5).

2. The method as claimed in claim 1, wherein at the step (3), a purified dermis fat and Type I Collagenase are mixed, a fat layer of an upper layer is removed from the dermis fat through centrifugation, and the stem cells are then separated and extracted from the dermis through centrifugation.

3. A method of manufacturing a composition for enlarging a penis, comprising the steps of:
   (1) partially anesthetizing an abdomen or flank region of a patient and then picking an auto-tissue of a skin of 200 cc by using an 8-9 gauge tube;
   (2) removing red blood cells of a lower layer from an auto-tissue of 200 g, picked at the step (1), through centrifugation for 3 minutes and then obtaining a purified mixture of 120 cc including a dermis and fat;
   (3) separating and extract stem cells of 4 cc by injecting Type I Collagenase of 1 g into the mixture of 80 cc including the dermis and fat, purified at the step (2) so that the Type I Collagenase of 1 g and the mixture of 80 cc are mixed;
   (4) picking blood of 20 cc from the patient and purifying the blood through centrifugation;
   (5) extracting a Platelet Rich Plasma (PRP) of 5 cc, including rich growth factors, from the blood purified at the step (4); and
   (6) manufacturing the composition for enlarging the penis by mixing the mixture of the dermis and fat of 40 cc obtained at the step (2), the stem cells of 4 cc obtained at the step (3), and the Platelet Rich Plasma (PRP) of 5 cc obtained at the step (5).

4. A method of enlarging a penis using a composition for enlarging the penis according to claim 3, the method comprising the steps of:
(1) incising a pubic area of a patient in a length of 1 cm or less up to a hypoderm layer;
(2) inserting a microtubule between an epidermis and a hypoderm of the incised part and moving the microtubule to a penis region;
(3) when an end of the microtubule is placed at the penis region, injecting the composition for enlarging the penis into the microtubule; and
(4) after the composition is injected, suturing the part incised at the step (1).

5. The method as claimed in claim 4, further comprising the step of first inserting an endoscope in order to check whether a nerve or a blood vessel vertically exists in a region of the epidermis and the hypoderm layer between which the microtubule is inserted.

\* \* \* \* \*